United States Patent [19]

Koga

[11] Patent Number: 5,364,564
[45] Date of Patent: Nov. 15, 1994

[54] PHOSPHATIDYL CHROMANOL DERIVATIVE, THE PRODUCTION METHOD THEREOF, ANTIOXIDANT AND EMULSIFIER

[75] Inventor: Takuro Koga, Noda, Japan
[73] Assignee: Noda Institute for Scientific Research, Japan
[21] Appl. No.: 190,479
[22] Filed: Feb. 2, 1994
[30] Foreign Application Priority Data Feb. 4, 1993 [JP] Japan .................. 5-039269

[51] Int. Cl.$^5$ ............... C07F 9/10; C07F 9/12
[52] U.S. Cl. ................... 252/351; 252/400.2; 549/220
[58] Field of Search ............... 549/220; 252/351, 400.2

[56] References Cited

U.S. PATENT DOCUMENTS 4,026,907  5/1977  Scott et al. ................ 549/407
5,011,964  4/1991  Mynarcik et al. ............ 558/179

FOREIGN PATENT DOCUMENTS 4-117392  4/1992  Japan .

OTHER PUBLICATIONS

Greene et al.; "Protective Groups in Organic Synthesis", 2nd ed., 1991, pp. 10–13.
Nagao, et al., "2F2p18 Synthesis and Antioxidant Activity of Vitamine C–Phospholipid Derivative," *Nippon Nogeikagaku Kaishi*, 64(3):245 (1990), English abstract.
Hildebrand, et al., "Phospholipids Plus Tocopherols Incrase Soybean Oil Stability", *JAOCS*, 61(3):552–555 (1984).

*Primary Examiner*—Johann Richter
*Assistant Examiner*—Michael B. Hydorn
*Attorney, Agent, or Firm*—Banner, Birch, McKie & Beckett

[57] ABSTRACT

The present invention relates to a phosphatidyl chromanol derivative having the formula:

wherein $R_1$ and $R_2$ represent a hydrogen atom, or a saturated or unsaturated fatty acid residue of 2–24 carbon numbers, n is an integer of 1–5 and X is a monovalent cation; a process for synthesizing the phosphatidyl chromanol derivative of the formula (3) which comprises reacting a phospholipid with a chroman derivative of the formula:

wherein n is an integer of 1–5 using a phospholipase D and an antioxidant/emulsifier containing the compound of the formula (3).

11 Claims, No Drawings

PHOSPHATIDYL CHROMANOL DERIVATIVE, THE PRODUCTION METHOD THEREOF, ANTIOXIDANT AND EMULSIFIER

FIELD OF THE INVENTION

The present invention relates to a novel phosphatidyl chromanol derivative, the production method thereof, antioxidant and emusifier containing same.

DESCRIPTIONS OF THE PRIOR ART

Phospholipids are widely present as constitutional components of the living body. The molecules include a hydrophobic portion and hydrophilic portion and which have amphiphatic nature. They are widely used as a natural emulsifier (surfactant) mainly in the food industry.

Moreover, various physiological and nutritional functions thereof are noted and the utilization in the field of pharmaceuticals and cosmetics have been researched for those having not only an emulsifying property, but also having various functional properties.

Vitamin E (tocopherols) is a potent antioxidant as an oil soluble radical-scavenger. Its antioxidant activity is very dependent on reactivity of hydrogen in OH group at 6-position on the chroman ring and it scavenges the reactive radical in materials very quickly to stabilize them. From such facts, Vitamin E has been used as an excellent natural antioxidant for foodstuffs, cosmetics and pharmaceuticals, especially for increasing the oxidative stability of edible oils in the food industry.

Additionally, it is known that the mere mixture of Vitamin E and phospholipid may show antioxidant activity (so-called synergistic effect) stronger than that of Vitamin E (see D. H. Hildebrand et. al., J. Am. Oil Chem. Soc. (JAOCS), Vol. 61, 552, 1984).

However, the use of Vitamin E or Vitamin E/phospholipid does not always result in sufficient antioxidation to oil/fat and more excellent antioxidants are being required accordingly.

SUMMARY OF THE INVENTION

The object of the present invention is to provide new compounds which are useful as an antioxidant having conspicuous antioxidant property as compared with conventional ones and additionally as an emulsifier, and the production method thereof.

The present inventors have made extensive research for achieving the object mentioned above. As a result, they have found that new phosphatidyl chromanol derivatives obtained by reacting a phospholipid with a specified chroman derivative in which an alcoholic hydroxyl group have been substituted at 2-position on the chroman ring may possess very excellent antioxidant property and emulsifying property additionally, and the derivatives may be synthesized from a phospholipid and a chroman derivative by transphosphatidylation reaction of phospholipase D under mild conditions with high conversion ratio.

Therefore, the subject of the present invention is to provide the following features: (a) A phosphatidyl chromanol derivative having an ester linkage between a phospholic acid of phospholipid and an alcoholic hydroxyl group at 2-position in a chroman derivative of the formula (1):

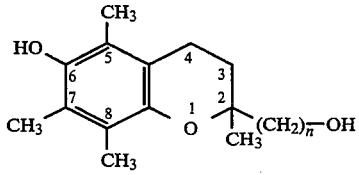

wherein n is an integer of 1-5.

(b) A phosphatidyl chromanol derivative of the formula (3):

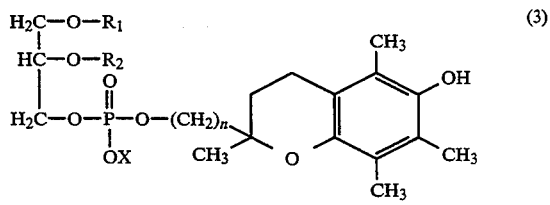

wherein $R_1$ and $R_2$, which may be identical or different, represent a hydrogen or, a saturated or unsaturated fatty acid residue having 2-24 carbon numbers, X is a monovalent cation and n is an integer of 1-5, having an ester linkage between a phospholic acid of glycerophospholipid of the formula (2):

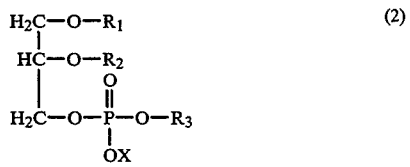

wherein $R_1$ and $R_2$, which may be identical or different, represent a hydrogen atom, or a saturated or unsaturated fatty acid residue of 2-24 carbons, $R_3$ represents a hydrogen or an organic residue in which one hydroxy group of base having hydroxy groups is removed, and X is a monovalent cation, and an alchoholic hydroxy group at 2-position in a chroman derivative of the formula (1)

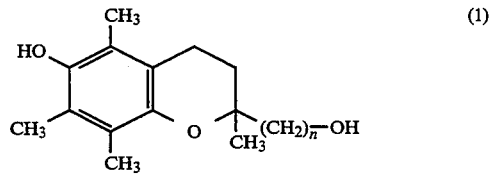

wherein n is an integer of 1-5.

(c) A process for synthesizing a phosphatidyl chromanol derivative as defined in said (a) which comprises esterifying a phospholic acid of phospholipid with an alcoholic hydroxy group at 2-position in chroman derivative of the formula (1):

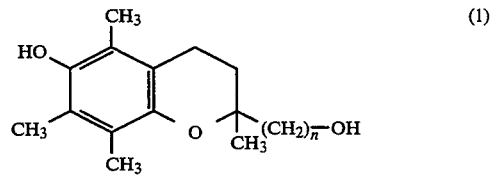

wherein n is an integer of 1-5.

(d) A process for synthesizing a phosphatidyl chromanol derivative as defined in said (a) which comprises reacting a phospholipid with a chroman derivative of the formula (1) using a phospholipase D.

(e) A process for synthesizing a phosphatidyl chromanol derivative of the formula (3):

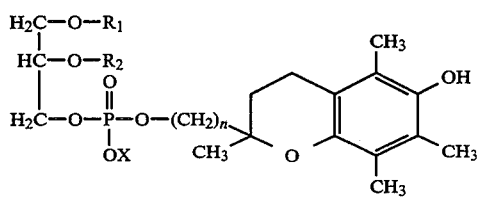

wherein $R_1$ and $R_2$, which may be identical or different, represent a hydrogen atom or, a saturated or unsaturated fatty acid residue having 2-24 carbons, X is a monovalent cation and n is an integer of 1-5 which comprises esterifying a phospholic acid of at least one of glycerophospholipids having the formula (2):

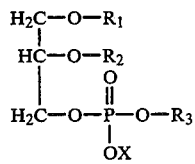

wherein $R_1$ and $R_2$, which may be identical or different, represent a hydrogen, or a saturated or unsaturated fatty acid residue of 2-24 carbons, $R_3$ represents a hydrogen or an organic residue in which one hydroxy group of base having hydroxy groups is removed, and X is a monovalent cation, with an alchoholic hydroxy group at 2-position in chroman derivative of the formula (1)

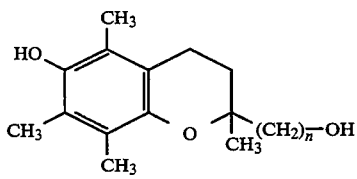

wherein n is an integer of 1-5, using a phospholipase D.

(f) An antioxidant comprising as an active ingredient at least one phosphatidyl chromanol derivative as defined in said (b) and (g) An emulsifier comprising as an active ingredient at least one phosphatidyl chromanol derivative as defined in said (b).

DESCRIPTION OF THE PREFERRED EMBODIMENTS

The present invention will be written in detail.

Firstly, the new phosphatidyl chromanot derivatives of the present invention are the products having an ester linkage between a phospholic acid of the phospholipid and an alcoholic hydroxyl group at 2-position in the chroman derivative of the formula (1) and particularly the phosphatidyl chromanol derivative of the formula (3) is preferred.

In the formula (1), the numbers on the chroman ring show the position according to the nomenclature. The phosphatidyl chromanol derivative of the formula (3) was designated by attaching the symbol "'" on the corresponding numbers.

Moreover, in the formula (3), $R_1$ and $R_2$, which may be identical or different, represent hydrogen or a saturated or unsaturated fatty acid residue having 2-24 carbons. In the formula (3), additionally, X is a monovalent cation, for example, a hydrogen, an alkali metal such as potassium and sodium, ammonia, an organic amine such as triethanol amine, or a basic amino acid such as lysine and arginine.

The phospholipid may be glycerophospholipids or sphingophospholipids which may be a chemically synthetic one or naturally-occurring one. Above all, the glycerophospholipid of the formula (2) is preferred and may be single compound or a mixture.

The fatty acid residue for $R_1$ and $R_2$ may be a saturated or unsaturated fatty acid residue having 2-24 carbons, for example, lauric, myristic, palmitmc, palmitoleic, stearic, oleic, linoleic, linolenic, arachidonic, eicosapentaenoic or docosahexaenoic acid having 10 to 22 of carbon numbers are preferred (llauric and myristic residues being $C_{11}H_{23}CO$— or $C_{13}H_{27}CO$—, respectively). In view of shelf stability of the claimed compound per se, saturation for the fatty acid residue of $R_1$ and $R_2$ is preferred and it is preferable that unsaturated group is previously treated for example with hydrogenation.

$R_3$ may be hydrogen or an organic residue in which OH group is removed from a base having hydroxyl groups, for example —$(CH_2)_2N^+(CH_3)_3$ (choline residue), —$(CH_2)_2NH_2$ (ethanolamine residue), —$CH_2CH(NH_2)COOH$ (serine residue), —$C_6H_6(OH)_5$ (inositol residue), —$CH_2CH(OH)CH_2(OH)$ (glycerol residue) and —H (hydrogen) being preferred.

Furthermore, especially preferred as phospholipids are phosphatidyl choline, phosphatidyl ethanolamine, phosphatidyl serine, phosphatidyl inositol, phosphatidyl glycerol and phosphatidic acid, or mixture thereof. Egg yolk lecithin or soybean lecithin produced from egg yolk or soybean is a mixture of various phospholipids which is most preferred for the present invention. Other natural phospholipids such as rapeseed lecithin, corn lecithin and safflower lecithin or modified lecithin such as lysolecithin and modified lecithin are also preferred.

In the chroman derivative of the formula (1), n is an integer of 1-5, preferably 1-3. 2,5,7,8-tetramethyl-6-hydroxy-2-hydroxymethyl-chroman and 2,5,7,8-tetramethyl-6-hydroxy-2-hydroxyethyl-chroman wherein n is 1 or 2 are especially preferred. These chroman derivatives may be either commercially available ones or chemically synthetic ones (see Richard Barner et. al., Helv. Chim. Acta, Vol. 62, 2384, 1979; Patent Kokai Nos. 56-145282, 58-201775 and 61-210029).

As mentioned above, the claimed new phosphatidyl chromanol derivative is the product having an ester linkage between a phospholic acid of the phospholipids and an alcoholic OH group at 2-position in the chroman derivative of the formula (1). For example, the phosphatidyl chromanol derivative synthesized from phospholipids have a saturated fatty acid residue at 1- and 2-positions of the glycero skeleton and chroman derivative is 2,5,7,8-tetramethyl6-hydroxy-2-hydroxymethyl-chroman, the following compounds may be exemplified and "—GPMC" therein is an abbreviation of "-sn-glycero-3-phospho-2'-hydroxymethyl-2',5',7',8'-tetramethyl-6'-hydroxy-chroman": 1,2-dilauroyl-GPMC; 1,2-dimyristoyl-GPMC; 1,2-dipalmitoyl-GPMC; 1,2-distearoyl-GPMC; 1-myKistoyl-2-palmitoyl-GPMC; 1-myristoyl-2-stearoyl-GPMC; 1-palmitoyi-2-myristoyl-GPMC; 1-palmitoyl-2-stearoyl-GPMC; 1-stearoyl-2-myristoyl-GPMC; and 1-stearoyl-2-palmitoyl-GPMC, and salts thereof.

Where the chroman derivative is 2,5,7,8-tetramethyl-6-hydroxy-2-hydroxyethyl-chroman, compounds as listed above may be shown similarly, except that "GPMC" is substituted with "-sn-glycero-3-phospho-2'-hydroxyethyl-2',5',7',8'-tetramethyl-6'-hydroxychroman".

The esterification in the production method of the claimed phosphatidyl chromanol derivative may be achieved according to chemical process (chemical synthetic process) or enzymatic process (converting reaction), especially, an enzymatic process using a phospholipase D is preferred.

If the esterification is carried out by the transphosphatidylation reaction using a phospholipase D, the claimed compounds may be synthesized under mild condition with high conversion ratio.

The phospholipase D used in the present invention may be any one having transphosphatidylation reaction, for example, one from *Streptomyces lydicus* (Honen Corporation), one from Streptomyces sp. (Phospholipase D Type VII of Sigma) and one from *Streptomyces chromofucus* (Baeringer Manheim Yamanouchi).

Next, the enzymatic process for producing the claimed phosphatidyl chromanol derivative will be written:

The reaction system for carrying out the enzymatic reaction may be in aqueous, in organic solvent or in mixed system.

The reaction product containing the preferred compounds of the present invention may be obtained by dissolving or suspending the phospholipid and the chroman derivative (1) in a solvent in a molar ratio of 1:1 to 1:10, adding phospholipase D in 0.1-100 units/ml (reaction solution) and carrying out the transphosphatidylation reaction (esterification) under appropriate condition while stirring.

The solvents used in this reaction may be any one, if they can dissolve or suspend the phospholipids and do not inhibit the enzymatic activity, for example, n-hexane, cyclohexane, diethylether, chloroform, ethyl acetate, acetonitrile, tert-butanol and mixture thereof are preferred.

The conditions for the enzymatic reaction are not limited if the condition in which the phospholipase D acts is used. It is a matter that optimal condition for phospholipase D used may be adopted. In generally, pH 2-10, preferably pH 4-7, a temperature of 5°-80° C., preferably 10°-50° C. and 10 minutes-100 hours, preferably 30 minutes-60 hours are adopted. When Phospholipase D Type VII manufactured by Sigma is used, for example, as a phospholipase D, the conditions for this enzymatic reaction are pH 3-8, preferably pH 5-6, 15 minutes-48 hours, preferably 1-10 hours and 10°-50° C., preferably 20°-40° C.

The phosphatidyl chromanol derivative obtained via this enzymatic reaction may be purified according to conventional methods. For example, the object product is firstly extracted using solvents such as mixed chloroform/methanol and hexane, the extracts are subject to chromatography and/or solvent fractionation and a highly purified product may be obtained. Column chromatography or thin layer chromatography may be used as the chromatography. Hydrophobic carrier such as silica gel is preferably used as a carrier for column chromatography.

The claimed phosphatidyl chromanol derivative is very useful for antioxidant and emulsifier and may be useful, for example, in foodstuffs, cosmetics and pharmaceuticals. In this case, this derivative may be used in its crude state or pure state and may be used as it is or as a solution or suspension in a solvent such as water, methanol and ethanol, alternatively it may be used as a powder with or without an excipient such as sugars.

Particularly, the claimed phosphatidyl chromanol derivative has a very strong antioxidant activity. That is, although the chroman derivative per se of the formula (1) possesses antioxidant activity, the claimed derivative has conspicuous activity over the derivative and additionally as compared with Vitamin E or mere mixture of Vitamin E and phospholipid, which is well known as an antioxidant.

A substance and a process in which the claimed antioxidant is to be used are not limited, but this oil soluble antioxidant may be most preferably used in edible fats/oils and other fatty foods. The amount of the antioxidant added is 0.001-1% (w/w), preferably 0.01-0.1% (w/w). When it is used in cosmetics such as cream, milk lotion, toilet water, make-up powder, oil and ointment, the amount thereof is 0.01-10% (w/w), preferably 0.5-5% (w/w).

Moreover, the claimed phosphatidyl chromanol derivative possesses an emulsifying activity in combination that the starting phospholipid has in nature and may be used alone or in combination with other emulsifiers as an emulsifier having antioxidant activity. Thus, the phosphatidyl chromanol derivative of the present invention has both antioxidant and emulsifying activities and may act effectively on even a substance which is apt to be oxidized in an emulsion as an antioxidant.

The claimed emulsifier may be used in chocolate, margarine, bread, cakes, biscuits, candies and the like in 0.001-5% (w/w), preferably 0.01-1% (w/w).

EXAMPLE 1

To 50 mg (73.8 $\mu$ mol) of commercially available dimyristoyl-L-$\alpha$-phosphatidyl choline (Sigma) and 20 mg (84.6 $\mu$ mol) of 2'5'7'8'-tetramethyl'-6-hydroxy-2-hydroxymethyl-chroman (manufactured by Kuraray) was added 1 ml of diethylether and then 24 ml of 0.01M citric acid buffer containing 0.01M of $CaCl_2$ (pH 6.0) was added in the resulting suspension. After incubation of the mixture for 5 minutes at 37° C. and 1 ml of an enzyme liquid containing 30 units of commercially available phospholipase D (Sigma, Phospholipase D Type VII) was added therein and the mixture was reacted at 37° C. for 2 hours while stirring. This reaction product was analyzed with HPLC and the conversion rate into the desired compound (rate of the formed objective product to phospholipid used) was as much as 95%.

The resulting reaction product was extracted with chloroform:methanol (2:1), adsorbed on a silica gel column and additionally eluted with chloroform: methanol (95:5). The eluate was dried under vacuum pressure to obtain 35 mg (43.2 $\mu$ mol, yield 58.5%) of the objective compound.

This compound was developed on TLC using silica gel plate (Silica Gel 60,Merck), with chloroform:methanol=80:20. As a result, single spot (Rf=0.43) showing red color (the presence of chroman ring) by exposing to ferric chloride/bathophenanthroline reagent (Tsugo T., Yamauchi K. and Kanno C., Nippon Nogeikagaku Kaishi, Vol. 42, 367–377, 1968) and blue color by exposing to Dittmer's reagent (the presence of phosphorus) (Dittmer J. D. and Lester R. L., J. Lipid Res., Vol. 5, 126–127, 1964) was detected. These facts demonstrated the formation of a compound having both phospholipid and chroman ring in its molecule.

Mass spectrum (SIMS), $^1$H-NMR spectrum and IR spectrum of this compound are as follows:

SIMS spectrum: m/z=849 (M+K$^+$)

$^1$H-NMR spectrum: [CDCl$_3$/CD$_3$OD (2:1, v/v), TMS as internal standard]: $\sigma$(ppm) 0.89 (6H, t, J=6.4 Hz), 1.27 (43H, br.s), 1.60 (4H, m), 1.83 (2H, m), 2.06 (3H, s), 2.12 (3H, s), 2.15 (3H, s), 2.30 (4H, t, J=6.4 Hz), 2.64 (2H, t, J=6.8 Hz), 3.84 (2H, m), 3.99 (2H, m), 4.16 (1H, m), 4.35 (1H, m), 5.22 (1H, m).

IR spectrum (KBr disk) (cm$^{-1}$): 3482, 2924, 853, 1745, 1457, 1246, 1027.

From these results, it was confirmed that this compound obtained by the enzymatic reaction of phospholipase D is a product linkaged between phospholic acid of the phospholipid and alcoholic OH group in the chroman derivative (a product by transphosphatidylation reaction) and is 1,2-dimyristoyl-sn-glycero-3-phospho-2'-hydroxymethyl-5',7',8'-tetramethyl-6'-hydroxy-chroman wherein R$_1$=R$_2$=myristic acid residue (C$_{13}$H$_{27}$CO—), n=1, X=K$^+$ in the formula (3).

EXAMPLE 2

Thirty-five mg (42.4 $\mu$ mol, yield 57.5%) of the objective compound was obtained similarly to Example 1, except that 20 mg (80.0 $\mu$ mol) of 2,5,7,8-tetramethyl-6-hydroxy-2-hydroxyethyl-chroman (manufactured by Kuraray) was used instead of 2,5,7,8-tetramethyl-6-hydroxy-2-hydroxymethyl-chroman.

The reaction product before purification was analyzed with HPLC and it was found that the conversion rate into the objective compound was 95%.

This product was developed on TLC using silica gel plate with chloroform:methanol=80:20 as a developing solution and a single spot (Rf=0.48) showing a red color and a blue color by exposing to ferric chloride/bathophenanthroline reagent and Dittmer's reagent, respectively, was detected. This fact demonstrated the formation of a compound having both the phospholipid and chroman ring in its molecule.

Mass spectrum (SIMS), $^1$H-NMR spectrum and IR spectrum of this compound are as follows:

SIMS spectrum:m/z=825 (M+H$^+$).

$^1$H-NMR spectrum: [CDCl$_3$/CD$_3$OD(2:1, v/v), TMS as internal standard]: $\sigma$(ppm) 0.89 (6H, t, J=6.7 Hz), 1.27 (43H, br.s), 1.60 (4H, m), 1.83 (2H, t, j=6.8Hz), 1.97 (2H, m), 2.07 (3H, s), 2.11 (3H, s), 2.15 (3H, s), 2.31 (4H, t, J=7.4 Hz), 2.62 (2H, t, J=6.8 Hz), 3.96 (2H, t, J=6.8 Hz), 4.11 (2H, m), 4.15 (1H, dd, J=12.0, 6.5 Hz), 4.39 (1H, dd, J=12.0, 3.5 Hz), 5.22 (1H, m).

IR spectrum (KBr disk) (cm$^{-1}$): 3482, 2924, 2853, 1745, 1457, 1246, 1027.

From these results, it was confirmed that this compound obtained by enzymatic reaction using the phospholipase D is a product linkaged between phospholic acid of the phospholipid and alcoholic OH group in the chroman derivative (a product by transphosphatidylation reaction) and is 1,2-dimyristoyl-sn-glycero-3-phospho-2'-hydroxyethyl-2',5',7',8'-tetramethyl-6'-hydroxy-chroman wherein R$_1$=R$_2$R=myristic acid residue, n=2, X=H$^+$ in the formula (3).

EXAMPLE 3

To 1g of L-$\alpha$-phosphatidylcholine (from egg yolk, Sigma) (1.29 mmol as average molecular weight 777) and 400 mg (1.69 mmol) of 2,5,7,8-tetramethyl-6-hydroxy-2-hydroxymethyl-chroman manufactured by Kuraray was added 20 ml of diethylether and the mixture was suspended, 480 ml of 0.01M citric acid buffer <pH 6.0) containing 0.01M of CaCl$_2$ was added in the suspension followed by incubation at 37° C. An enzymatic liquid 20 ml containing 600 units of commercially available phospholipase D (Sigma, Phospholipase D Type VII) was added therein with stirring and the reaction was carried out at 37° C. for 2 hours. This reaction product was analyzed with HPLC and the conversion rate into the objective compound was as much as 95%.

The resulting product was purified similarly to Example 1 to obtain 0.82 g (0.90 mmol, yield 69.8%) of 1,2-diacyl-sn-glycero-3-phospho-2'-hydroxymethyl-2',5',7',8'-tetramethyl-6'-hydroxy-chroman.

This product was developed on TLC using silica gel plate with chloroform:methanol=80:20 as a developing solution. As a result, a single spot (Rf=0.43) showing a red color and a blue color by exposing to ferric chloride/bathophenanthroline reagent and Dittmer's reagent, respectively, was detected. This fact demonstrated that this product obtained by enzymatic reaction using phospholipase D is a compound having both phospholipid and chroman ring in its molecule and is a product linkaged between phospholic acid of the phospholipid and alcoholic OH group in the chroman derivative (a product by transphosphatidylation reaction).

EXAMPLE 4

The objective 1,2-diacyl-sn-glycero-3- phospho-2'-hydroxyethyl-2',5',7',8'-tetramethyl-6'-hydroxy-chroman hydroxy-chroman 0.86 g (0.93 mmol, yield 72.1%) was prepared similarly to Example 3, except that 400 mg (1.60 mmol) of 2,5,7,8-tetramethyl-6-hydroxy-2-hydroxyethyl-chroman manufactured by Kuraray was used instead of 2,5,7,8-tetramethyl-6-hydroxy-2-hydroxymethyl-chroman.

The reaction product before purification was analyzed with HPLC and the conversion rate into the objective compound was 95%.

This product was developed on TLC using silica gel plate with chloroform:methanol=80:20 as a developing solution. A single spot (Rf=0.48) showed a red color and a blue color by exposing to ferric chloride/bathophenanthroline reagent and Dittmer's reagent, respectively. This fact demonstrated that this product obtained by enzymatic reaction using phospholipase D is a compound having both phospholipid and chroman ring in its molecule and is a product linkaged between phospholic acid of the phospholipid and alcoholic OH group in the chroman derivative (a product by transphosphatidylation reaction).

EXAMPLE 5

To 50 mg of phospholipids as listed in Table and 20 mg (84.6 $\mu$mol) of 2,5,7,8-tetramethyl-6-hydroxy-2-hydroxymethyl-chroman manufactured by Kuraray was added 1 ml of diethylether and the mixture was suspended, 24 ml of 0.01M citric acid buffer (pH 6.0) containing 0.01M CaCl$_2$ was added in the suspension followed by incubation at 37° C. After that, an enzyme liquid 1 ml containing 30 units of commercially available phospholipase D (Sigma, Phospholipase D Type VII) was added in therein and the mixture was reacted at 37° C. for 2 hours while stirring. The respective reaction products were analyzed with HPLC and the conversion rate into these compounds was high as shown in Table 1.

Each resulting reaction product was purified similarly to Example 1 to obtain various phosphatidyl chromanol derivatives (1,2-diacyl-sn- glycero-3-phospho-2'-hydroxymethyl-2',5',7',8'-tetramethyl-6'-hydroxy-chroman) in yield as shown in Table 1.

TABLE 1

| Phospholipids | Objective Product | |
|---|---|---|
| | Conversion (%) | Yield (mg) |
| Phosphatidyl choline (from soybean, Sigma) | 95 | 32.0 |
| Phosphatidyl choline (from pig liver, Funakoshi) | 94 | 32.5 |
| Soybean lecithin (Tokyo Kasei) | 82 | 22.5 |
| Egg yolk lecithin (Tokyo Kasei) | 90 | 28.5 |
| Phosphatidyl ethanolamine (from pig liver, Funakoshi) | 93 | 30.0 |
| Phosphatidyl serine (from bovine brain, Funakoshi) | 94 | 31.5 |

These products were developed on TLC using silica gel plate with chloroform:methanol=80:20 as a developing solution. In each product, single spot (Rf=0.43) showing a red color and a blue color by exposing to ferric chloride/bathophenanthroline reagent and Dittmer's reagent, respectively, was detected. These facts demonstrated that these compounds obtained by enzymatic reaction with phospholipase D are compounds having both phospholipid and chroman ring in their molecule and are products linkaged between phospholic acid of the phospholipids and alcoholic OH groups in the chroman derivatives (products by transphosphatidylation reaction).

EXAMPLE 6

The various phosphatidyl chromanol derivatives (1,2-diacyl-sn-glycero-3-phospho-2'-hydroxyethyl-2',5',7',8'-tetramethyl-6'-hydroxy-chroman) were prepared similarly to Example 5 in yield as shown in Table 2, except that 20 mg (80.0 $\mu$ mol) of 2,5,7,8-tetramethyl-6-hydroxy-2-hydroxyethyl-chroman manufactured by Kuraray was used instead of 2,5,7,8-tetramethyl-6-hydroxy-2-hydroxymethyl-chroman.

Each product before purification was analyzed with HPLC and the conversion rate into the objective products was high as in Table 2.

TABLE 2

| Phospholipids | Objective Product | |
|---|---|---|
| | Conversion (%) | Yield (mg) |
| Phosphatidyl choline (from soybean, Sigma) | 97 | 34.0 |
| Phosphatidyl choline (from pig liver, Funakoshi) | 97 | 34.5 |
| Soybean lecithin (Tokyo Kasei) | 80 | 24.5 |
| Egg yolk lecithin (Tokyo Kasei) | 91 | 28.5 |
| Phosphatidyl ethanolamine (from pig liver, Funakoshi) | 95 | 32.0 |
| Phosphatidyl serine (from bovine brain, Funakoshi) | 95 | 32.0 |

TABLE 2-continued

| Phospholipids | Objective Product | |
|---|---|---|
| | Conversion (%) | Yield (mg) |
| bovine brain, Funakoshi) | | |

These products were developed on TLC using silica gel plate with chloroform:methanol=80:20 as a developing solution. In each case, single spot /R#=0.48) showing a red color and a blue color by exposing to ferric chloride/bathophenanthroline reagent and Dittmer's reagent, respectively, was detected. These facts demonstrated that these products obtained by enzymatic reaction with phospholipase D are compounds having both phospholipid and chroman ring in their molecule and are products linkaged between phospholic acid of the phospholipid and alcoholic OH group in the chroman derivative (products by transphosphatidylation reaction).

EXAMPLE 7

The comparison of the following compounds on antioxidant activity was carried out: the phosphatidyl chromanol derivatives (abbreviated as PMC and PEC mn Table 3, respectively) of the present invention obtained by Examples 3 and 4; the phosphatidyl chromanol derivatives (abbreviated as SPMC and SPEC in Table 3, respectively) of the present invention obtained similarly to Examples 5 and 6 using soybean lecithin of Tokyo Kasei as a phospholipid; the chroman derivative (abbreviated as MC and EC in Table 3, respectively) used in Example 3 or 5 and Example 4 or 6; and conventional antioxidant and/or phospholipid.

To 1.0 g of pure lard (Tsukishima Food) in a glass petri dish was admixed 0.4 μmol of each product shown in Table 3 (the phosphatidyl chromanol derivative of the present invention and phospholipid were determined on phosphorus). The mixture was stored at 60° C. in the dark condition and the weight gain was recorded every day to detect the degree of oxidation of lard. The term to which the weight of the lard increases is referred to the end of induction period and the result thereof is shown in Table 3.

TABLE 3

| Test compounds | Oxydation inhibiting period |
|---|---|
| PMC (the Invention) | 720 hours (30 days) |
| PEC (the Invention) | 720 hours (30 days) |
| SPMC (the Invention) | 720 hours (30 days) |
| SPEC (the Invention) | 720 hours (30 days) |
| MC | 360 hours (15 days) |
| EC | 360 hours (15 days) |
| Vitamin E (D-α-tocopherol, Eisai) | 384 hours (16 days) |
| L-α-phosphatidyl choline (from egg yolk, Sigma) | 192 hours (8 days) |
| Equimolar mixture of Vitamin E and L-α-phosphatidyl choline | 480 hours (20 days) |
| No addition | 240 hours (10 days) |

Note: Data shown in the Table are average value of two experiments

Table 3 shows that the induction period with the phosphatidyl chromanol derivatives of the present invention is extremely longer than conventional Vitamin E (D-α-tocopherol) and equimolar mixture of Vitamin E and L-α-phosphatidyl choline from egg yolk which is known to act as a synergist with vitamin E. In short, it was found that the derivatives may possess a very high antioxidant property. In addition, the antioxidant property of the present phosphatidyl chromanol derivative was found to be extremely excellent as compared with chromanol derivative.

EXAMPLE 8

The emulsifying activity of the present phosphatidyl chromanol derivatives (abbreviated as PMC and PEC in Table 4, respectively) obtained by Examples 3 and 4, the present phosphatidyl chromanol derivatives (abbreviated as SPMC and SPEC in Table 4, respectively) obtained similarly to Examples 5 and 6 using soybean lecithin of Tokyo Kasei as phospholipid, and phospholipid was determined according to the procedure described in Journal of Agricultural and Food Chemistry, Vol. 26, 716, 1978.

That is, to every 0.1 g of various products as listed in Table 4 was added 20 ml of water and the mixture was homogenized at 10,000 rpm for 30 seconds using a homogenizer CH 6010 of Kinematika and at 10,000 rpm for additional 1 minute while adding gradually 1 g of soybean oil to prepare an emulsion. Each emulsion immediately after emulsification, and after incubation at 25° C. for 72 hours after emulsification were diluted 200 times with aqueous 0.1% Triton X-100 solution and the diluted emulsion was determined at absorbance of 500 nm. Table 4 shows the results.

TABLE 4

| Test products | Absorbence (500 nm) | |
| --- | --- | --- |
| | Immediately after emulsfication | After 72 hours |
| PMC (the Invention) | 0.51 | 0.42 |
| PEC (the Invention) | 0.52 | 0.43 |
| SPMC (the Invention) | 0.50 | 0.41 |
| SPEC (the Invention) | 0.50 | 0.43 |
| L-α-phosphatidyl choline (from egg yolk, Sigma) | 0.52 | 0.43 |
| No addition | 0.31 | — |

Note: Data shown in the Table are average values of two experiments

In Table 4, the liquid with no addition of test product separated oil completely after 72 hour-incubation, but no separation oil was appreciated on other sections. From Table 4, the emulsifying activity of the present phosphatidyl chromanol derivative has clearly the same as that of L-α-phosphatidyl choline which is known as an emulsifier.

I claim:

1. A phosphatidyl chromanol derivative of the formula (3):

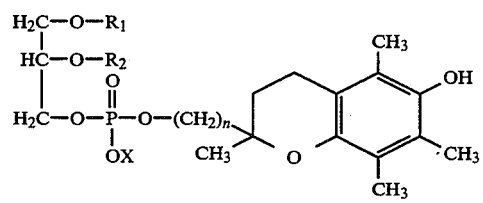

wherein $R_1$ and $R_2$, which may be identical or different, represent a hydrogen atom or, a saturated or unsaturated fatty acid residue having 2-24 carbons, X is a monovalent cation and n is an integer of 1-5, .

2. A derivative according to claim 1 wherein $R_1$ and $R_2$ are hydrogen or a fatty acid residue of 10-22 carbon numbers.

3. A derivative according to claim 3 wherein $R_1$ and $R_2$ are a fatty acid residue selected from a group consisting of lauric, myristic, palmitic, palmitoleic, stearic, oleic, linoleic, linolenic, arachidonic, eicosapentaenoic and docosahexaenoic acids.

4. A derivative according to claim 1 wherein the glycerophospholipid moiety is selected from phosphatidyl choline, phosphatidyl ethanolamine, phosphatidyl serine, phosphatidyl inositol, phosphatidyl glycerol and phosphatidic acid.

5. A derivative according to claim 1 wherein the glycerophospholipid moiety is phosphatidyl choline.

6. A derivative according to claim 1 wherein X is hydrogen, an alkali metal, organic amine or basic amino acid.

7. A derivative according to claim 1 wherein n is 1–2.

8. A derivative according to claim 1 wherein the glycerophospholipid moiety is derived from egg yolk lecithin, soybean lecithin, rapeseed lecithin, corn lecithin, safflower lecithin or modified lecithin.

9. A derivative according to claim 1 which is 1,2-dilauroyl-sn-glycero-3-phospho-2'-hydroxymethyl-2',5',7',8'-tetramethyl-6'-hydroxy-chroman; 1,2-dimyristoyl-sn-glycero-3-phospho-2'-hydroxymethyl-2',5',7',8'-tetramethyl-6'-hydroxy-chroman; 1,2-dipalmitoyl-sn-glycero-3-phospho-2'-hydroxymethyl-2',5',7',8'-tetramethyl-6'-hydroxy-chroman; 1,2-distearoyl-sn-glycero-3-phospho-2'-hydroxymethyl-2',5',7',8'-tetramethyl-6'-hydroxy-chroman; 1,2-diarachidonoyl-sn-glycero-3-phospho-2'-hydroxymethyl-2',5',7',8'-tetramethyl-6'-hydroxy-chroman; 1-myristoyl-2-palmitoyl-sn-glycero-3-phospho-2'-hydroxymethyl-2',5',7',8'-tetramethyl-6'-hydroxychroman; 1-myristoyl-2-stearoyl-sn-glycero-3-phospho-2'-hydroxymethyl-2',5',7',8'-tetramethyl-6'-hydroxychroman; 1-palmitoyl-2-myristoyl-sn-glycero-3-phospho-2'-hydroxymethyl-2,',5',7',8'-tetramethyl-6'-hydroxychroman; 1-palmitoyl-2-stearoyl-sn-glycero-3-phospho-2'-hydroxymethyl-2',5',7',8'-tetramethyl-6'-hydroxychroman; 1-stearoyl-2-myristoyl-sn-glycero-3-phospho-2'-hydroxymethyl-2',5',7',8'-tetramethyl-6'-hydroxychroman; 1-stearoyl-2-palmitoyl-sn-glycero-3-phospho-2'-hydroxymethyl-2',5',7',8'-tetramethyl-6'-hydroxychroman; 1,2-dilauroyl-sn-glycero-3-phospho-2'-hydroxyethyl-2',5',7',8'-tetramethyl-6'-hydroxy-chroman; 1,2-dimyristoyl-sn-glycero-3-phospho-2'-hydroxyethyl-2',5',7',8'-tetramethyl-6-hydroxy-chroman; 1,2-dipalmitoyl-sn-glycero-3-phospho-2'-hydroxyethyl-2',5',7',8'-tetramethyl-6-hydroxy-chroman; 1,2-distearoyl-sn-glycero-3-phospho-2'-hydroxyethyl-2',5',7',8'-tetramethyl-6-hydroxy-chroman; 1,2-diarachidonoyl-sn-glycero-3-phospho-2'-hydroxyethyl-2',5',7',8'-tetramethyl-6-hydroxy-chroman; 1-myristoyl-2-palmitoyl-sn-glycero-3-phospho-2'-hydroxyethyl-2',5',7',8'-tetramethyl-6-hydroxy-chroman; 1-myristoyl-2-stearoyl-sn-glycero-3-phospho-2'-hydroxyethyl-2',5',7',8'-tetramethyl-6-hydroxy-chroman; 1-palmitoyl-2-myristoyl-sn-glycero-3-phospho-2'-hydroxyethyl-2',5',7',8'-tetramethyl-6-hydroxy-chroman; 1-palmitoyl-2-stearoyl-sn-glycero-3-phospho-2'-hydroxyethyl-2',5',7',8'-tetramethyl-6-hydroxy-chroman; 1-stearoyl-2-myristoyl-sn-glycero-3-phospho-2'-hydroxyethyl-2,40 ,5',7',8'-tetramethyl-6-hydroxy-chroman; 1-stearoyl-2-palmitoyl-sn-glycero-3-phospho-2'-hydroxyethyl-2',5',7',8'-tetramethyl-6-hydroxy-chroman; or salts thereof.

10. An antioxidant comprising as active ingredient at least one phosphatidyl chromanol derivative as claimed in claim 1.

11. An emulsifier comprising as active ingredient at least one phosphatidyl chromanol derivative as claimed in claim 1.

* * * * *